United States Patent [19]

Kahn et al.

[11] 4,203,515
[45] May 20, 1980

[54] DENTAL CAP PACKAGE

[75] Inventors: Henry Kahn, 1724 Grand Bahama West, Palm Springs, Calif. 92262; Sidney M. Libit, Glencoe, Ill.

[73] Assignee: Henry Kahn, Palm Springs, Calif.

[21] Appl. No.: 932,510

[22] Filed: Aug. 10, 1978

[51] Int. Cl.² ............... B65D 81/00; A61C 5/08
[52] U.S. Cl. ............................ 206/63.5; 206/820; 433/218
[58] Field of Search ............... 206/461, 820, 63.5; 32/12

[56] References Cited

U.S. PATENT DOCUMENTS

| 3,548,506 | 12/1970 | Harrington | 206/820 |
| 3,586,161 | 6/1971 | Fong et al. | 206/820 |
| 3,949,476 | 4/1976 | Hahn | 32/12 |

*Primary Examiner*—William T. Dixson, Jr.

[57] ABSTRACT

A package for holding a supply of small articles of assorted shapes to be conveniently dispensed singly, having features enabling one or more articles to be separated from the package while leaving the remainder undisturbed.

3 Claims, 5 Drawing Figures

U.S. Patent      May 20, 1980      4,203,515
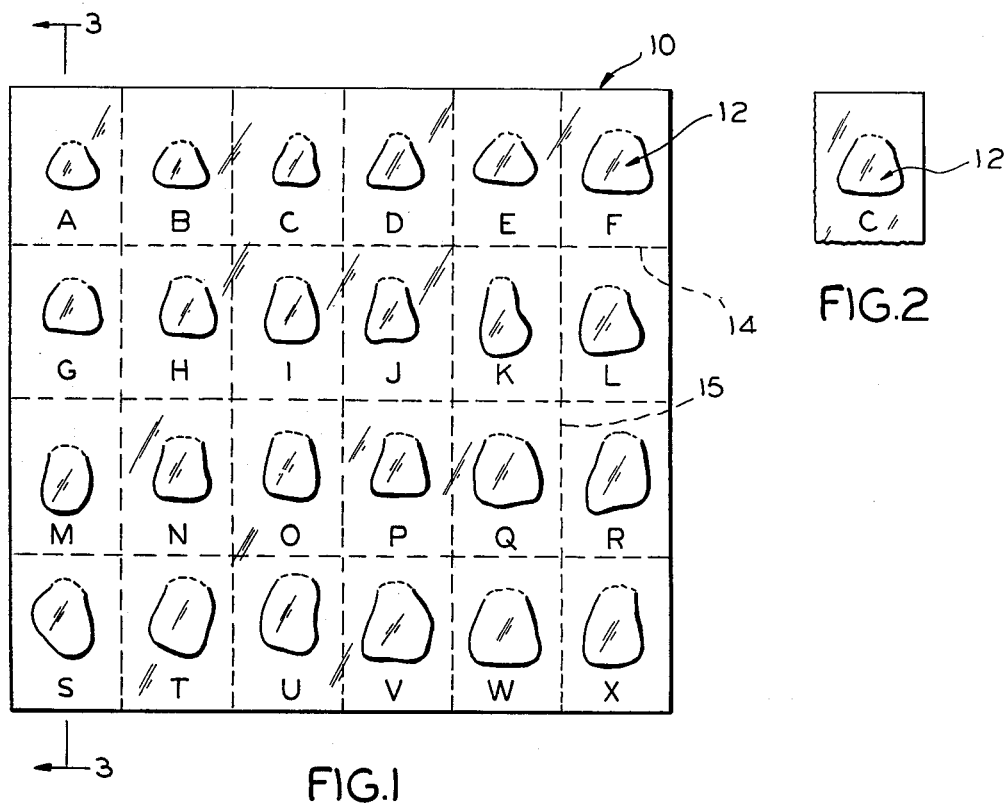
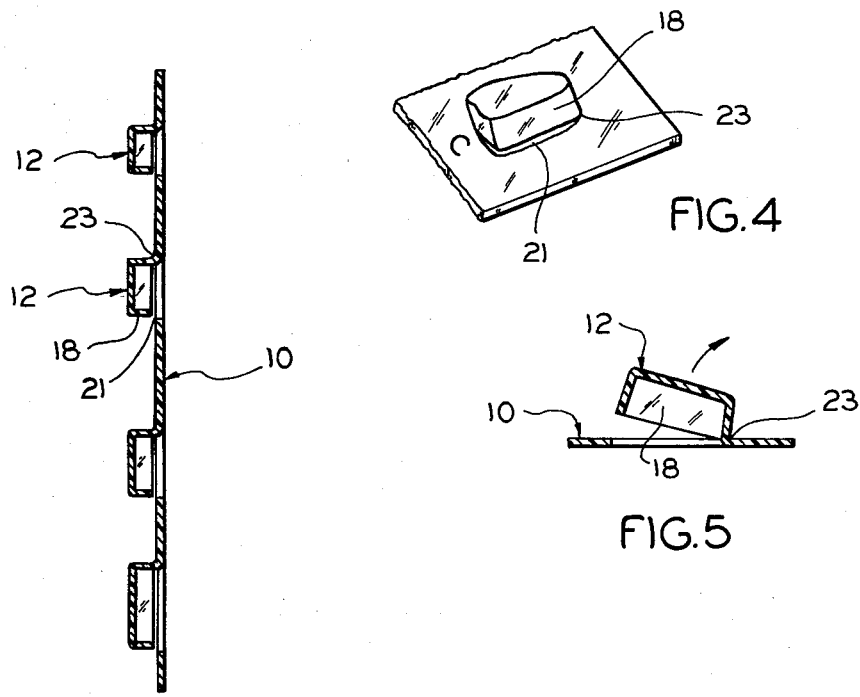

DENTAL CAP PACKAGE

BACKGROUND AND SUMMARY OF THE INVENTION

The present invention is basically intended for use with pre-molded dental caps. For example, of the kind disclosed in U.S. Pat. No. 3,949,476, issued Apr. 13, 1976. In that patent there is described and shown a cup-shaped object or shell of plastics material manufactured in various shapes and sizes and adapted for use, for example, in the fabrication of dental crowns by means of techniques disclosed in said patent. For a better understanding of the disclosure herein suffice it to mention that the invention shell comprises a depressed portion, i.e. a cup, bordered by a flange. Since the caps are desirably made commercially available in many sizes and shapes, a number is assigned to each different configuration. Thus, the flange has a two-fold advantage: as a place for reliable handling of the cap while making the crown, and to receive a number serving as immediate identification.

As a practical matter the dentist will find it practically mandatory to maintain a reasonable supply of these caps and, therefore, in accordance with the invention, there is provided a base sheet having some convenient number of depressions, i.e. cups of various shapes and sizes arranged for easy access and separation from the package.

In accordance with the invention I provide a base sheet of an easily sheared plastics material in which the plurality of cup-shaped depressions are formed, as by vacuum forming. The shape of the depressions will embrace a desired range of shapes and sizes.

In another aspect the plurality of depressions may be arranged substantially equidistantly and the base sheet then scored or otherwise divided off by perforations or other lines of weakness to facilitate the removal of a selected cap by tearing.

Viewed in another way, the area of the base sheet intermediate the lines of weakness is, in effect, a flange, and may be availed of as a convenient place to grip the object with tweezers. Moreover, the flange may be used to receive identification, e.g. the name or monogram of the manufacturer or source, as well as letters or numberals, serving to identify the objects, e.g. the approximate transverse dimension of a cap.

SUMMARY OF THE INVENTION

The invention will be disclosed in connection with a set or assortment of various cup-shaped devices useful in the practice of dentistry, for example, the fabrication of crowns as shown and described in said patent. The plastics material from which the mold for the crown is desirably formed, is transparent, light in weight, tenacious, reasonably rigid and machinable, e.g. a methylmethacrylate, acetate or material of equivalent characteristics.

Inasmuch as the operator will be confronted with a large variety of applications, it is desirable that a reasonably large assortment be made available as a kit. It will be evident that expedition dictates an arrangement in compact, orderly form. To this end the invention comprises a working assortment of cup-like elements made, as by vacuum forming, out of a flat blank. In this way a sufficient portion of the blank is made available to be used as a flange, e.g. handle, to facilitate manipulation of the element in the manner described in said patent. The characteristics of the material may be so selected as to enable cutting with scissors.

The cup-shaped element is desirably fabricated in a manner to facilitate separation thereof from the base, as by providing a line of weakness at the junction thereof, preferably only part way around the same. Thus, when the operator is ready to effect separation of a selected element, the desired element may be simply torn from the base sheet. Those portions of the base sheet circumjacent the cup-shaped elements may bear indicia identifying each of the several sizes of elements.

BRIEF DESCRIPTION OF THE DRAWING

FIG. 1 is a top plan view of one embodiment of the invention;

FIG. 2 is a top plan view of one of the elements separated from the remainder;

FIG. 3 is a cross section taken on the line 3—3 of FIG. 1;

FIG. 4 is a perspective view of the element of FIG. 2 showing the cup in the as-molded condition;

FIG. 5 shows the element in the process of being detached from the base panel.

DESCRIPTION OF THE PREFERRED EMBODIMENT

In a preferred form the invention comprises a panel 10, sometimes herein referred to as the "base panel" of some plastics composition which is thin enough to be reasonably rigid under its conditions of use, tenacious, to avoid cracking, and capable of being vacuum-formed to provide the plurality of cup-shaped elements 12 (FIGS. 1 and 2). The plurality of shapes and sizes illustrated are typical of an assortment which the practitioner is likely to be called upon to use. A typical assortment may be 24 in number. The panel 10 may be perforated along intersecting lines 14 and 15 or other lines of weakness or may be without such lines, as preferred. The result is shown in FIG. 2.

Following forming, the elements are desirably to be readily detached for use. To this end the perpendicular wall 18 of the element is separated over the greater part of its extent by a slit 21, leaving the element still attached over the remainder of such extent by a neck 23. The neck 23 serves not only as a "tear" zone but will anchor the rest of the elements 12 in a position convenient of access. The neck 23 is desirably perforated in order to facilitate tearing of the same.

We claim:

1. A package of cup-shaped shells in various shapes and sizes used in fabrication of dental crowns comprising a base sheet of moldable plastic material having a plurality of said shells in longitudinal and lateral rows protruding from one surface of said sheet in substantially equally-spaced relationships to form a flange around each shell, said shells having walls perpendicular to said sheet and tops of differing dental configurations, the greater portion of the wall periphery of each shell at its juncture with the base sheet being separated therefrom, the remaining portion of said periphery remaining integral with said sheet along a line of weakness for ultimate removal of said shell from its flange, each flange carrying identification indicia for its respective shell and providing a handle for its use after detachment from said sheet.

2. The package according to claim 1 wherein said sheet has intersecting lines of weakness between said rows for separation of said flanges from said sheet.

3. A package of cup-shaped shells in various shapes and sizes used in fabrication of dental crowns comprising a base sheet of moldable plastic material having a plurality of said shells in longitudinal and lateral rows protruding substantially evenly from one surface of said sheet in substantially equally-spaced relationships, intersecting lines of weakness between said rows for forming a flange around each shell, said shells having walls perpendicular to said sheet and flat tops of differing dental configurations, each flange carrying identification indicia for its respective shell and providing a handle for its use after detachment of said flange from said sheet, the greater portion of the wall periphery of each shell at its juncture with the base sheet being separated therefrom, the remaining portion of said periphery remaining integral with said sheet on a line of weakness for ultimate removal of said shell from its flange.

* * * * *